(12) United States Patent
Dupelle

(10) Patent No.: US 9,138,573 B2
(45) Date of Patent: Sep. 22, 2015

(54) EXTERNAL DEFIBRILLATORS, TRANSCUTANEOUS ELECTRODES FOR SAME, AND METHODS OF USE

(75) Inventor: Michael R. Dupelle, N. Attleboro, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 405 days.

(21) Appl. No.: 11/683,928

(22) Filed: Mar. 8, 2007

(65) Prior Publication Data

US 2008/0221631 A1    Sep. 11, 2008

Related U.S. Application Data

(60) Provisional application No. 60/893,557, filed on Mar. 7, 2007.

(51) Int. Cl.
*A61N 1/00* (2006.01)
*A61N 1/04* (2006.01)

(52) U.S. Cl.
CPC .............. *A61N 1/046* (2013.01); *A61N 1/0492* (2013.01); *A61N 1/048* (2013.01)

(58) Field of Classification Search
CPC ..... A61N 1/3962; A61N 1/3956; A61N 1/05; A61N 1/046
USPC ......................... 607/4–5, 115, 142
See application file for complete search history.

(56) References Cited

U.S. PATENT DOCUMENTS

| 1,212,541 | A | | 1/1917 | Morse |
| 1,662,446 | A | | 3/1928 | Wappler |
| 3,972,329 | A | | 8/1976 | Kaufman |
| 4,092,985 | A | | 6/1978 | Kaufman |
| 4,633,879 | A | * | 1/1987 | Ong ............................. 600/391 |
| 4,653,501 | A | * | 3/1987 | Cartmell et al. .............. 600/392 |
| 4,674,512 | A | | 6/1987 | Rolf |
| 4,763,660 | A | | 8/1988 | Kroll et al. |
| 4,777,954 | A | | 10/1988 | Keusch et al. |
| 4,779,630 | A | | 10/1988 | Scharnberg et al. |
| 4,838,273 | A | | 6/1989 | Cartmell |
| 5,330,526 | A | | 7/1994 | Fincke et al. |
| 5,356,428 | A | * | 10/1994 | Way ............................. 607/142 |

(Continued)

FOREIGN PATENT DOCUMENTS

WO    WO 93/21989    11/1993

OTHER PUBLICATIONS

"Biphasic Waveforms," IEEE Engineering in Medicine and Biology, Jun. 1990, p. 26.

(Continued)

*Primary Examiner* — Catherine Voorhees
*Assistant Examiner* — Roland Dinga
(74) *Attorney, Agent, or Firm* — Fish & Richardson P.C.

(57) ABSTRACT

An external defibrillator is provided including (a) a pair of disposable electrodes configured to be adhered to the skin of a patient, each electrode including an electrically conductive layer comprising a metal that is polarized during a defibrillating pulse, and (b) a control unit configured to deliver a defibrillating pulse to the patient through the electrodes. The waveform is configured to substantially depolarize the metal, and may be, for example, a biphasic waveform. Method of defibrillation and defibrillation electrodes are also provided.

3 Claims, 4 Drawing Sheets

(56) References Cited

U.S. PATENT DOCUMENTS

| | | |
|---|---|---|
| 5,427,096 A | 6/1995 | Bogusiewicz et al. |
| 5,700,281 A | 12/1997 | Brewer et al. |
| 5,769,872 A * | 6/1998 | Lopin et al. .................... 607/5 |
| 5,785,040 A * | 7/1998 | Axelgaard .................... 600/391 |
| 5,921,925 A | 7/1999 | Cartmell et al. |
| 5,951,598 A * | 9/1999 | Bishay et al. ................ 607/142 |
| 6,019,877 A | 2/2000 | Dupelle et al. ........... 204/196.11 |
| 6,076,002 A | 6/2000 | Cartmell et al. |
| 6,101,413 A * | 8/2000 | Olson et al. .................... 607/5 |
| 6,115,638 A * | 9/2000 | Groenke .................... 607/142 |
| 6,280,463 B1 | 8/2001 | Dupelle et al. ............... 607/142 |
| 6,564,079 B1 | 5/2003 | Cory et al. |
| 6,587,726 B2 | 7/2003 | Lurie et al. .................... 607/42 |
| 6,597,949 B1 * | 7/2003 | Dhurjaty .................... 607/5 |
| 6,714,824 B1 | 3/2004 | Ohta et al. |
| 2003/0004558 A1 * | 1/2003 | Gadsby .................... 607/142 |
| 2003/0233129 A1 | 12/2003 | Matos |
| 2004/0267325 A1 | 12/2004 | Geheb et al. |
| 2005/0107834 A1 * | 5/2005 | Freeman et al. .................... 607/5 |
| 2005/0131465 A1 | 6/2005 | Freeman et al. |
| 2006/0009809 A1 | 1/2006 | Marcovecchio et al. |
| 2006/0074284 A1 | 4/2006 | Juola et al. |
| 2006/0074452 A1 * | 4/2006 | Dupelle et al. .................... 607/4 |
| 2008/0221631 A1 | 9/2008 | Dupelle |

OTHER PUBLICATIONS

McAdams, Chapter 3—Biomedical Electrodes for Biopotential Monitoring and Electrostimulation, pp. 31-124, H.-J. Yoo, C. van Hoof (eds.), Bio-Medical CMOS ICs, Springer Science & Business Media, LLC (2011).

* cited by examiner

EXTERNAL DEFIBRILLATORS, TRANSCUTANEOUS ELECTRODES FOR SAME, AND METHODS OF USE

CROSS-REFERENCE TO RELATED APPLICATIONS

This application claims priority to U.S. Provisional Application Ser. No. 60/893,557, filed on Mar. 7, 2007.

TECHNICAL FIELD

This invention relates to external defibrillators, transcutaneous electrodes for such defibrillators, and methods of using such defibrillators.

BACKGROUND

External defibrillators frequently include a pair of "hands-free" disposable electrodes, which are essentially flexible pads that are adhered to the skin of a patient having a cardiac event (i.e., used transcutaneously). By "hands-free," we mean electrodes of the type that are adhered to a patient, rather than paddles that are held by a rescuer during defibrillation. Hands-free disposable electrodes typically include a metal layer, formed from a thin sheet of metal or a conductive ink printed on a substrate, and a liquid or solid electrically conductive gel covering the metal layer so that electrical current passes through the gel to the patient's body. The metal layer may be, for example, tin or silver-silver chloride.

It is important that the material used in the metal layer depolarize quickly (within seconds) after a defibrillating pulse ("shock") is delivered to a patient. Otherwise, the electrode is not capable of sensing a signal that will allow the defibrillator to generate a clear ECG and determine whether another shock should be delivered within a short period of time.

SUMMARY

It is been observed that, when stainless steel is used as the conductive metal layer in a defibrillating electrode, the metal layer may become polarized after the defibrillating pulse is applied and then depolarize only slowly. In such cases, depolarization generally occurs too slowly for a clear ECG to be obtained sufficiently quickly. Certain other metals also exhibit this behavior. Polarization may be due to a build-up of electrical charge at the interface between the metal layer and the gel.

The inventor has discovered that stainless steel, and other metals that polarize during a defibrillating pulse, can be used as the conductive metal layer, provided that the defibrillator with which the electrode is used is configured to deliver to the patient a defibrillation waveform that is capable of rapidly depolarizing the electrode. Stainless steel is an advantageous material for the conductive layer, as it is resistant to corrosion, thereby providing a long electrode shelf life. Stainless steel is also strong, and thus its use in the conductive layer reduces the likelihood that the electrode will be damaged by mishandling.

Depolarizing waveforms include biphasic waveforms, e.g., those which are discussed in detail in U.S. Pat. No. 5,769,872, the disclosure of which is incorporated herein by reference. While not wishing to be bound by theory, the inventor believes that the negative phase of a biphasic waveform reduces or eliminates the electrical charge, allowing the electrode to rapidly depolarize after the defibrillating pulse is delivered.

In one aspect, the invention features an external defibrillator comprising a pair of electrodes configured to be adhered to the skin of a patient, each electrode including an electrically conductive layer comprising a metal that polarizes during a defibrillating pulse, and a control unit configured to deliver a defibrillating pulse to the patient through the electrodes, the defibrillating pulse comprising a waveform configured to substantially depolarize the metal. By "substantially depolarize", we mean that polarization is eliminated, or reduced sufficiently so that a clear ECG can be read by the defibrillator.

The metal may comprise stainless steel. The waveform may comprise a biphasic waveform. Preferably, the electrodes are configured to monitor electrical signals from the patient's body, and the control unit is configured to generate an ECG from such signals. In some cases, the electrodes may include a reusable portion and a disposable portion.

In another aspect, the invention features a method of treating a patient with a defibrillating pulse, the method comprising (a) applying to the skin of the patient a pair of electrodes, each electrode including an electrically conductive layer that comprises a metal that polarizes during a defibrillating pulse, and (b) using an external defibrillator to deliver to the patient, through the electrodes, a defibrillating pulse in the form of a waveform that substantially depolarizes the metal.

Some implementations may include one or more of the following features. The metal may be stainless steel. The waveform may be a biphasic waveform. The method may further include monitoring electrical signals from the patient's body, using the same electrodes. The method may include generating an ECG from the signals, and using this information to determine whether a further pulse should be delivered to the patient. The method may include configuring the waveform to substantially depolarize the electrodes within 6 seconds of delivery of the pulse. The method may also include deciding, based on the ECG, whether to deliver a further defibrillating pulse to the patient.

In another aspect, the invention features a medical electrode comprising: (a) an electrode body, including a protective backing sheet, a coupling layer, and a portion configured to adhere the electrode to a patient's skin; (b) within the electrode body, an electrically conductive layer comprising a metal that polarizes during a defibrillating pulse; and (c) a cable configured to provide electrical communication between the electrode body and an external defibrillator. The electrode is configured to be used as a "hands-free" electrode and to deliver a defibrillating pulse to the patient. Preferred electrodes are configured to also monitor electrical signals from the patient's body, and to deliver a defibrillating pulse comprising a waveform configured to substantially depolarize the metal.

The invention also features electrodes that comprise a disposable portion, including a coupling assembly configured to couple the electrode to a patient's skin and including an electrically conductive gel, and a reusable portion, including an electrically conductive metal layer.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
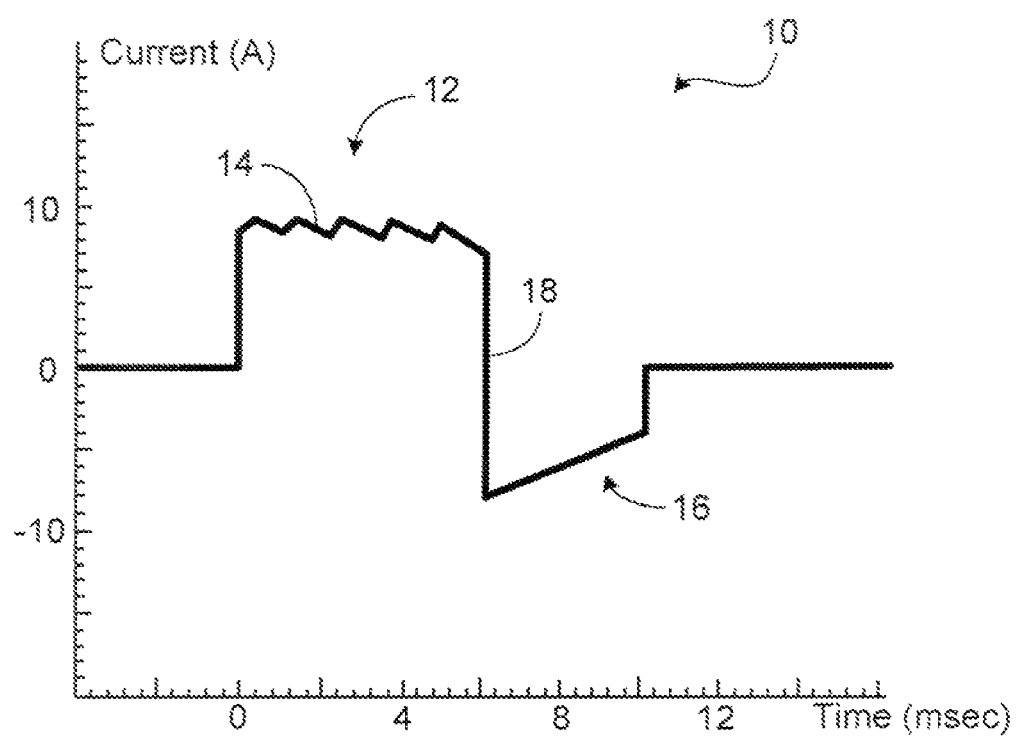
FIG. 1 is a diagram showing an example of a biphasic waveform.

An example of a biphasic waveform is shown in FIG. 1. The biphasic waveform 10 shown in FIG. 1 includes a generally rectilinear positive phase 12 having a sawtooth ripple 14. The current of the positive phase is approximately 9 amps. The positive phase has a duration of approximately 6 milliseconds. The positive phase is followed by a negative phase 16. The negative phase has a duration of approximately 4 milliseconds and has an initial current of approximately −8 amps. The transition 18 between the positive and negative phases is generally very short, e.g., 0.1 millisecond or less.

The waveform shown in FIG. 1 is simply one example of a suitable waveform. Other waveforms having different characteristics may be used, including both biphasic waveforms having other shapes and other types of waveforms, provided they are capable of depolarizing the electrode as discussed above.

Preferably, the waveform is selected to be capable of depolarizing the electrode (i.e., either completely depolarizing the electrode or reducing the polarization to a level where a clean ECG can be obtained) within a few seconds, e.g., 4-6 seconds of less, after the pulse is delivered. This allows the rescuer to continue treatment on a patient without interruption. The waveform may be generated in any desired manner, e.g., using the circuitry described in U.S. Pat. No. 5,769,872. Referring to FIG. 3 herein, which is a reproduction of FIG. 2 of U.S. Pat. No. 5,769,872, a storage capacitor 20' (115 µF) is charged to a maximum of 2200 volts by a charging circuit 22' while relays 26' and 28' and the H-bridge are open, and then the electric charge stored in storage capacitor 20' is allowed to pass through electrodes 21' and 23' and the body of a patient 24'. In particular, relay switches 17' and 19' are opened, and then relay switches 26' and 28' are closed. Then electronic switches 30', 32', 34', and 36' of H-bridge 48' are closed to allow the electric current to pass through the patient's body in one direction, after which electronic H-bridge switches 30', 32', 34', and 36' are opened and H-bridge switches 38', 40', 42', and 44' are closed to allow the electric current to pass through the patient's body in the opposite direction. Electronic switches 30'-44' are controlled by signals from respective opto-isolators, which are in turn controlled by signals from a microprocessor 46', or alternatively a hard-wired processor circuit. Relay switches 26', and 28', which are also controlled by microprocessor 46', isolate patient 24' from leakage currents of bridge switches 30'-44', which may be about 500 micro-amps. Relay switches 26' and 28' may be relatively inexpensive because they do not have to "hot switch" the current pulse. They close a few milliseconds before H-bridge 48' is "fired" by closure of some of the H-bridge switches.

Optionally, a resistive circuit 50 that includes series-connected resistors 52, 54, and 56 is provided in the current path, each of the resistors being connected in parallel with a shorting switch 58, 60, and 62 controlled by microprocessor 46. The resistors are of unequal value, stepped in a binary sequence to yield $2^n$ possible resistances where n is the number of resistors. During the initial "sensing pulse," when H-bridge switches 30', 32', 34', and 36' are closed, all of the resistor-shorting switches 58, 60, and 62 are in an open state so that the current passes through all of the resistors in series. Current-sensing transformer 64 senses the current passing through the patient 24', from which microprocessor 46 determines the resistance of the patient 24'.

Figure 2:
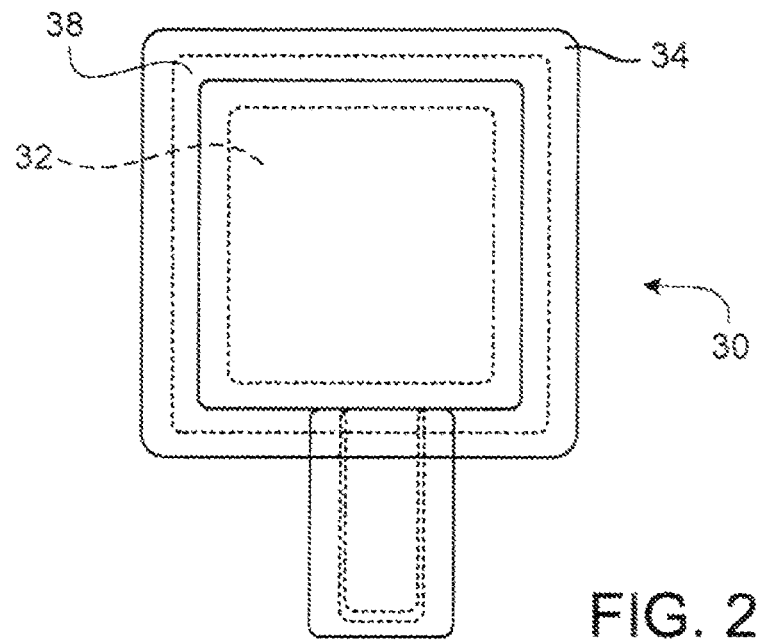
FIG. 2 is a front view.
Figure 2A:
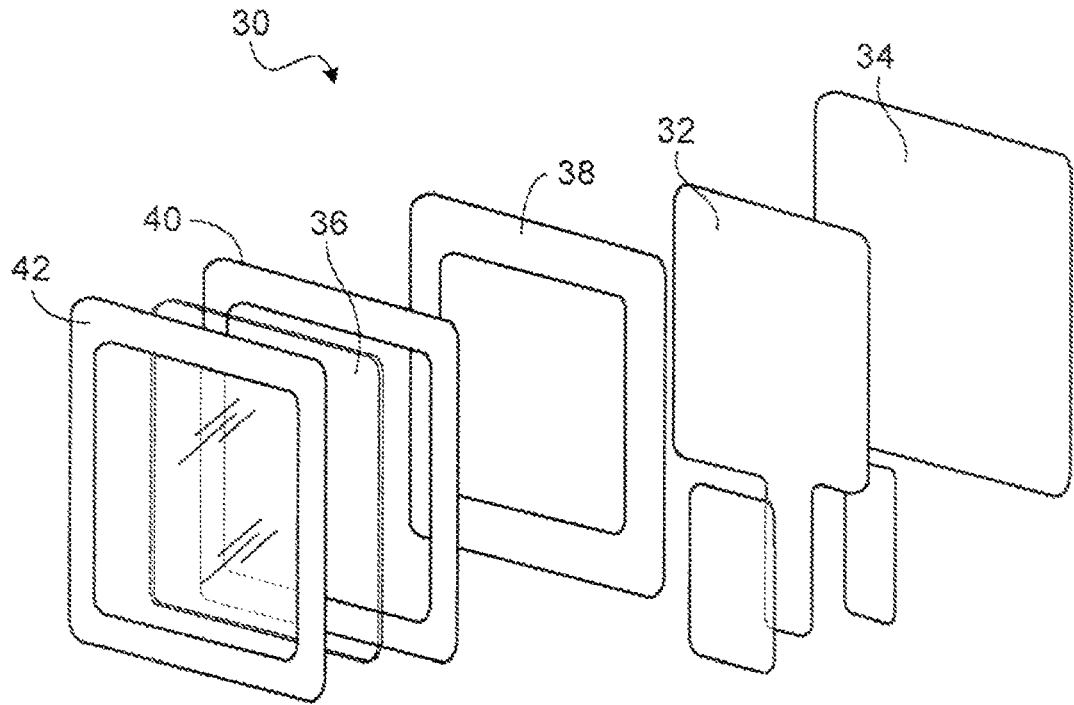
FIG. 2A is an exploded view showing the layers of an electrode according to one implementation.
Figure 3:
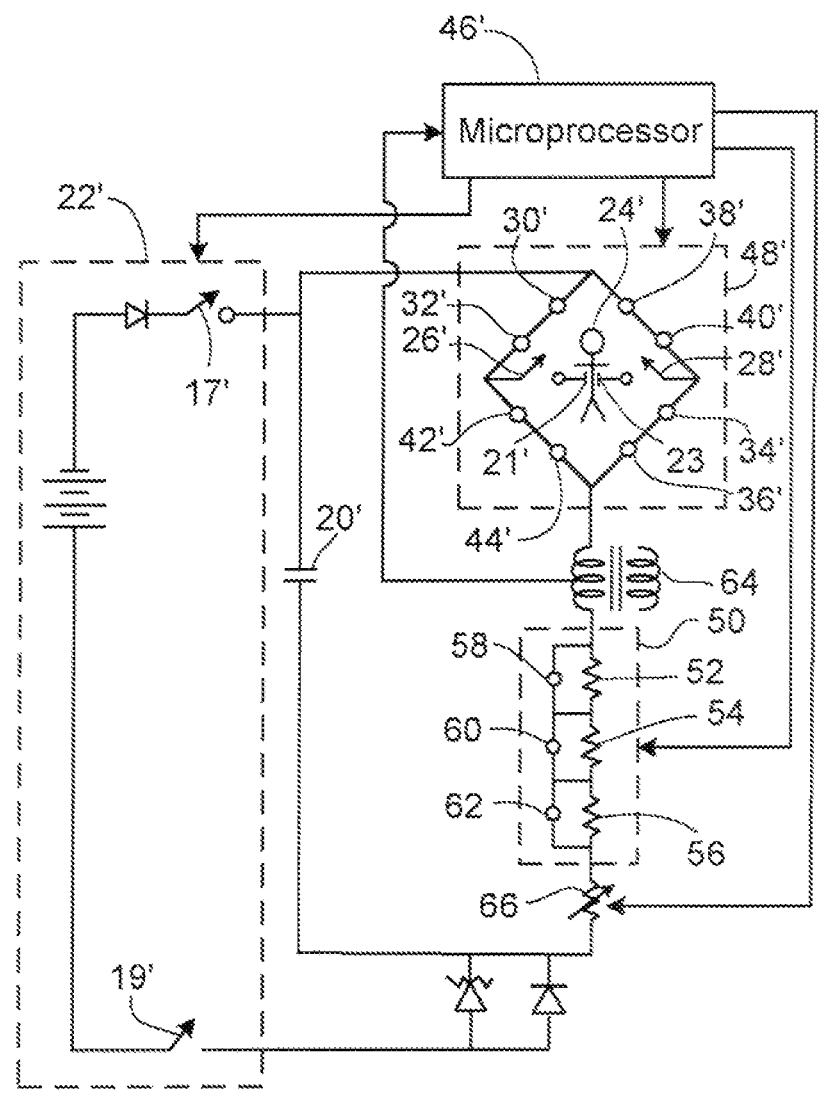
FIG. 3 is a diagram showing a circuit suitable for generating the waveform shown in FIG. 1.

As shown in FIGS. 2 and 2A, an electrode 30 includes a very thin and non-rigid stainless steel conductive layer 32. In some implementations, the conductive layer is thin enough to be radiolucent, e.g., less than about 0.001" thick. Typically, the conductive layer is from about 0.002" to about 0.004" thick. The conductive layer 32 has a surface area that is sufficiently large for defibrillation or cardioversion.

Suitable stainless steel alloys include, for example, 302, 316, and alloys having similar composition. Other alloys may be used.

A non-conductive, protective backing layer 34 (e.g., of vinyl or other flexible plastic) is disposed on one side of the conductive layer, while a coupling layer 36 is disposed on the opposite (patient) side. A mask 38 is provided between the coupling layer and conductive layer. The coupling layer is sandwiched between a conductive ring 40 and an adhesive ring 42, configured to adhere the electrode to a patient's skin. The coupling layer, conductive ring and adhesive ring together form a modular coupling assembly. The coupling assembly is generally configured to be disposable, i.e., to be discarded after a single use. For example, conductive ring 40 may include a pressure sensitive adhesive that releasably joins the coupling assembly to the mask 38. After a used coupling assembly is removed, it can be replaced by a new one, allowing the rest of the electrode to be re-used. In some cases, the rest of the electrode may be used for 100 uses or more.

The coupling layer 36 may be, for example, a high viscosity electrically conductive gel (often referred to as a "solid" gel or hydrogel), or a foam or sponge layer saturated with a liquid, electrically conductive gel.

Figure 4:
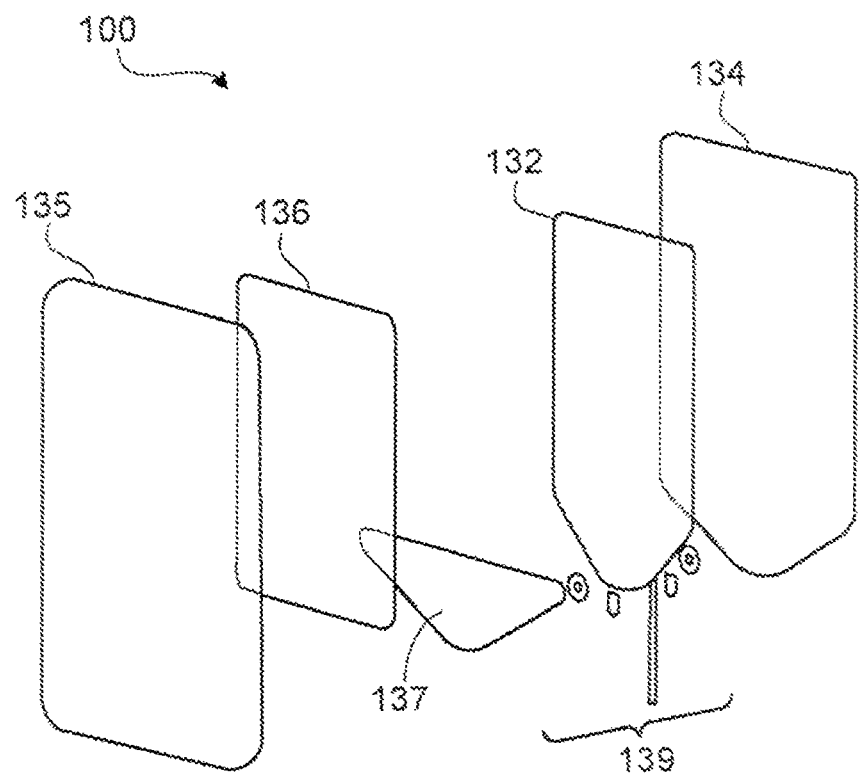
FIG. 4 is an exploded view showing the layers of an electrode according to an alternate implementation.

In another implementation, shown in FIG. 4, the conductive ring 40 and adhesive ring 42 are omitted. The electrode 100 includes a conductive layer 132, backing layer 134, and coupling layer 136. These components are similar to conductive layer 34, backing layer 34, and coupling layer 36 discussed above. In this case, the coupling layer is not replaceable, and thus the electrode is disposable after a single use. The electrode also includes a removable release sheet 135 which covers and protects the coupling layer 136 prior to use. An insulating layer 137 is used to insulate the connecting wire assembly 139.

The electrodes described herein are preferably configured to be a multi-purpose defibrillator electrode, i.e., capable of monitoring electrical signals from the patient, as well as defibrillation. For example, after a defibrillating pulse is delivered, the electrode is configured to monitor a signal that can be used to generate an ECG.

A number of embodiments of the invention have been described. Nevertheless, it will be understood that various modifications may be made without departing from the spirit and scope of the invention. For example, the conductive layer may comprise a different metal that polarizes during a defibrillating pulse, for example copper or aluminum.

Accordingly, other embodiments are within the scope of the following claims.

What is claimed is:

1. An external defibrillator comprising:
a pair of flexible electrodes configured to be adhesively secured to the skin of a patient, each electrode including a flexible electrically conductive layer comprising stainless steel that delivers the defibrillating pulse to the patient and that polarizes during delivery of the defibrillating pulse; and a control unit configured to deliver a defibrillating pulse to the patient through the electrodes, the defibrillating pulse comprising a waveform having at least two phases and being configured to substantially depolarize the stainless steel layer within about 6 seconds of delivery of the pulse to the patient, wherein the control unit is further configured to monitor electrical signals detected from the patient's body and generate an ECG after the defibrillating pulse is delivered.

2. The defibrillator of claim 1 wherein the electrodes comprise a disposable coupling portion and a reusable portion including the electrically conductive metal layer.

3. The defibrillator of claim 1 wherein the waveform comprises a biphasic waveform.

\* \* \* \* \*